(12) United States Patent
Gerst (10) Patent No.: US 7,954,515 B2
(45) Date of Patent: Jun. 7, 2011

(54) COMBINATION CAP AND PLUG ASSEMBLY

(75) Inventor: Patrick T. Gerst, Oakdale, MN (US)

(73) Assignee: Colder Products Company, St. Paul, MN (US)

( * ) Notice: Subject to any disclaimer, the term of this patent is extended or adjusted under 35 U.S.C. 154(b) by 125 days.

(21) Appl. No.: 12/541,288

(22) Filed: Aug. 14, 2009

(65) Prior Publication Data

US 2010/0006157 A1 Jan. 14, 2010

Related U.S. Application Data

(60) Provisional application No. 61/089,086, filed on Aug. 15, 2008.

(51) Int. Cl.
*F16L 55/10* (2006.01)
*B65D 55/16* (2006.01)

(52) U.S. Cl. ........ 138/89; 138/89.1; 138/89.2; 215/306; 220/375

(58) Field of Classification Search .................... 138/89, 138/89.1, 89.2; 215/306; 220/375
See application file for complete search history.

(56) References Cited

U.S. PATENT DOCUMENTS

| | | | | |
|---|---|---|---|---|
| 658,313 | A * | 9/1900 | Bernardi | 403/300 |
| 2,921,708 | A * | 1/1960 | Marcel | 215/230 |
| 3,199,707 | A * | 8/1965 | Folkman | 215/306 |
| 3,574,312 | A * | 4/1971 | Miller | 138/96 R |
| 3,948,290 | A * | 4/1976 | Arisland | 138/89 |
| 3,974,938 | A * | 8/1976 | Steadman | 220/266 |
| 3,987,930 | A * | 10/1976 | Fuson | 220/287 |
| 3,990,727 | A | 11/1976 | Gallagher | |
| 4,132,225 | A * | 1/1979 | Whattam | 600/576 |
| 4,342,337 | A * | 8/1982 | Underwood | 138/96 T |
| 4,661,110 | A * | 4/1987 | Fortier et al. | 604/256 |
| D293,710 | S | 1/1988 | Woods | |
| 4,844,512 | A | 7/1989 | Gahwiler | |
| D314,172 | S | 1/1991 | Whitley, II | |
| 4,991,882 | A | 2/1991 | Gahwiler | |
| D315,959 | S | 4/1991 | Bilangi | |
| 5,052,725 | A | 10/1991 | Meyer et al. | |
| 5,104,157 | A | 4/1992 | Bahner | |
| 5,213,376 | A | 5/1993 | Szabo | |
| D341,596 | S | 11/1993 | Stein | |
| 5,277,402 | A | 1/1994 | Szabo | |
| 5,324,080 | A | 6/1994 | McNaughton et al. | |

(Continued)

FOREIGN PATENT DOCUMENTS

EP 0 982 525 A1 3/2000

(Continued)

OTHER PUBLICATIONS

Exh. B, Hollister, admitted prior art as of the filing date of Jan. 28, 2009, 1 page.

(Continued)

*Primary Examiner* — Patrick F Brinson
(74) *Attorney, Agent, or Firm* — Merchant & Gould P.C.

(57) ABSTRACT

A combination cap and plug assembly. A cap portion of the assembly is used to stop flow of material through a male coupling, and a plug portion is used to stop flow of material through a female coupling. The combination cap and plug assembly includes a tether that allows the assembly to be coupled to hose or tubing that is connected to the male and female coupling.

4 Claims, 9 Drawing Sheets

U.S. PATENT DOCUMENTS

| | | | |
|---|---|---|---|
| 5,466,017 | A | 11/1995 | Szabo et al. |
| D368,304 | S | 3/1996 | Morrison |
| 5,568,946 | A | 10/1996 | Jackowski |
| D377,969 | S | 2/1997 | Grantham |
| D387,146 | S | 12/1997 | Morrison |
| D387,147 | S | 12/1997 | Vandermast et al. |
| D388,876 | S | 1/1998 | Sampson |
| 5,799,987 | A | 9/1998 | Sampson |
| 5,823,508 | A | 10/1998 | Nie |
| 5,873,610 | A | 2/1999 | Szabo |
| 5,964,485 | A | 10/1999 | Hame et al. |
| 5,992,895 | A | 11/1999 | Steinkamp |
| 6,036,672 | A * | 3/2000 | Allen et al. .............. 604/167.02 |
| 6,257,627 | B1 | 7/2001 | Fujiwara et al. |
| 6,688,654 | B2 | 2/2004 | Romero |
| 7,055,869 | B2 | 6/2006 | Malone |
| 7,163,028 | B1 * | 1/2007 | Atkinson et al. ................ 138/89 |
| 7,370,662 | B2 | 5/2008 | Mele |
| 7,377,553 | B2 | 5/2008 | Takayanagi |
| 7,448,653 | B2 | 11/2008 | Jensen et al. |
| D602,128 | S | 10/2009 | Williams et al. |
| 2006/0212024 | A1 | 9/2006 | Blake et al. |
| 2008/0073911 | A1 | 3/2008 | Wells et al. |
| 2009/0137979 | A1 | 5/2009 | Adair et al. |
| 2009/0188575 | A1 | 7/2009 | Williams et al. |

FOREIGN PATENT DOCUMENTS

| | | |
|---|---|---|
| GB | 2 323 418 A | 9/1998 |

OTHER PUBLICATIONS

Exh. C, Hollister, admitted prior art as of the filing date of Jan. 28, 2009, 1 page.

Exh. E, Hollister, admitted prior art as of the filing date of Jan. 28, 2009, 1 page.

Exh. A, Hollister, Ostomy Care, admitted prior art as of the filing date of Jan. 28, 2009, 1 page.

Exh. D, Hollister, Ostomy Care, admitted prior art as of the filing date of Jan. 28, 2009, 1 page.

International Search Report and Written Opinion mailed Jun. 5, 2009.

U.S. Appl. No. 29/331,581, filed Jan. 28, 2009.

* cited by examiner

COMBINATION CAP AND PLUG ASSEMBLY

RELATED APPLICATIONS

This application claims the benefit of U.S. patent application Ser. No. 61/089,086 filed on Aug. 15, 2008, the entirety of which is hereby incorporated by reference.

This application relates to U.S. patent application Ser. No. 61/024,044 filed on Jan. 28, 2008 and U.S. patent application Ser. No. 61/040,045 filed on Mar. 27, 2008, the entireties of which are hereby incorporated by reference.

BACKGROUND

Coupling assemblies typically include female and male couplings that are connected to create a fluid flow path therebetween. Such coupling assemblies can be used in various applications, including biomedical applications, beverage dispensing, instrument connections, photochemical handling, etc.

Some coupling assemblies include valve assemblies that stop fluid flow through the male and female couplings when the couplings are disconnected. Other coupling assemblies are non-valved. In non-valved coupling assemblies, the couplings remain open when the male coupling is disconnected from the female coupling. Any material in the fluid flow path is therefore free to continue to flow out of the male and female couplings when disconnected.

SUMMARY

Example embodiments described herein relate to a combination cap and plug assembly. A cap portion of the assembly can be used to stop flow through a male coupling, and a plug portion can be used to stop flow through a female coupling. In examples shown herein, the combination cap and plug assembly includes a tether that allows the assembly to be coupled to hose or tubing that is connected to the male and/or female coupling.

The details of one or more techniques are set forth in the accompanying drawings and the description below. Other features, objects, and advantages of these techniques will be apparent from the description, drawings, and claims.

DETAILED DESCRIPTION

Example embodiments described herein relate to a combination cap and plug assembly. A cap portion of the assembly can be used to stop flow through a male coupling, and a plug portion can be used to stop flow through a female coupling. In examples shown herein, the combination cap and plug assembly includes a tether that allows the assembly to be coupled to hose tubing that is connected to the male and/or female coupling.

Referring now to FIGS. 1-5, an example cap and plug assembly 100 is shown. The assembly 100 includes a main body 102 with first and second ends 104, 106. A plug portion 120 extends from a first side 151 of the main body 102, and a cap portion 140 extends from a second side 153 of the main body 102, as described below.

In the example shown, the main body 102 has a contoured width to include thin portions 103 and thick portions 105. The thin portions 103 allow the main body 102 to flex more easily when the assembly 100 is in use. For example, when the assembly 100 is tethered to a hose as described below, the thin portions 103 allow the main body 102 to flex so that the plug portion 120 and the cap portion 140 can be inserted into male and/or female couplings. Other configurations for the main body 102, such as a constant width, can be used.

A tether 110 is connected to the first end 104 of the main body 102 of the assembly 100. The tether 110 includes a body 112 that forms an opening 113 that is sized to receive a tube 115 (see FIG. 2) that extends therethrough so that the assembly 100 is tethered to the tube 115. In example embodiments, the tube 115 is connected to a male or female coupling (see FIGS. 6-9 described below) so that the assembly 100 can be used to stop the flow through the male and/or female couplings.

Although the opening 113 is circular in the example shown, the size and/or shape of the opening 113 can be varied depending on the application. For example, the opening 113 can be oval, square, or rectangular in shape, if desired. In alternative embodiments, the opening 113 can include frictional members, such as small members that project from the body 112 into the opening 113 to help affix the tether 110 at a certain position on the tube 115. Other configurations are possible.

The plug portion 120 and the cap portion 140 are located adjacent to the second end 106 of the main body 102. A handle member 108 is also positioned at the second end 106. The handle member 108 allows a user to easily grasp the assembly 100 as the user inserts or removes the plug portion 120 and/or the cap portion 140 from a coupling, as described below.

The plug portion 120 includes a plug member 122 and an end member 126. A transition member 124 is positioned between the plug member 122 and the end member 126. In the example shown, the plug member 122 has a greater diameter than the end member 126. The diameter of both the plug member 122 and the end member 126 decrease slightly as the plug member 122 and the end member 126 extend away from the first side 151 of the main body 102. This tapering allows the plug member 122 and the end member 126 to be inserted into a female coupling, as described below.

Figure 1:
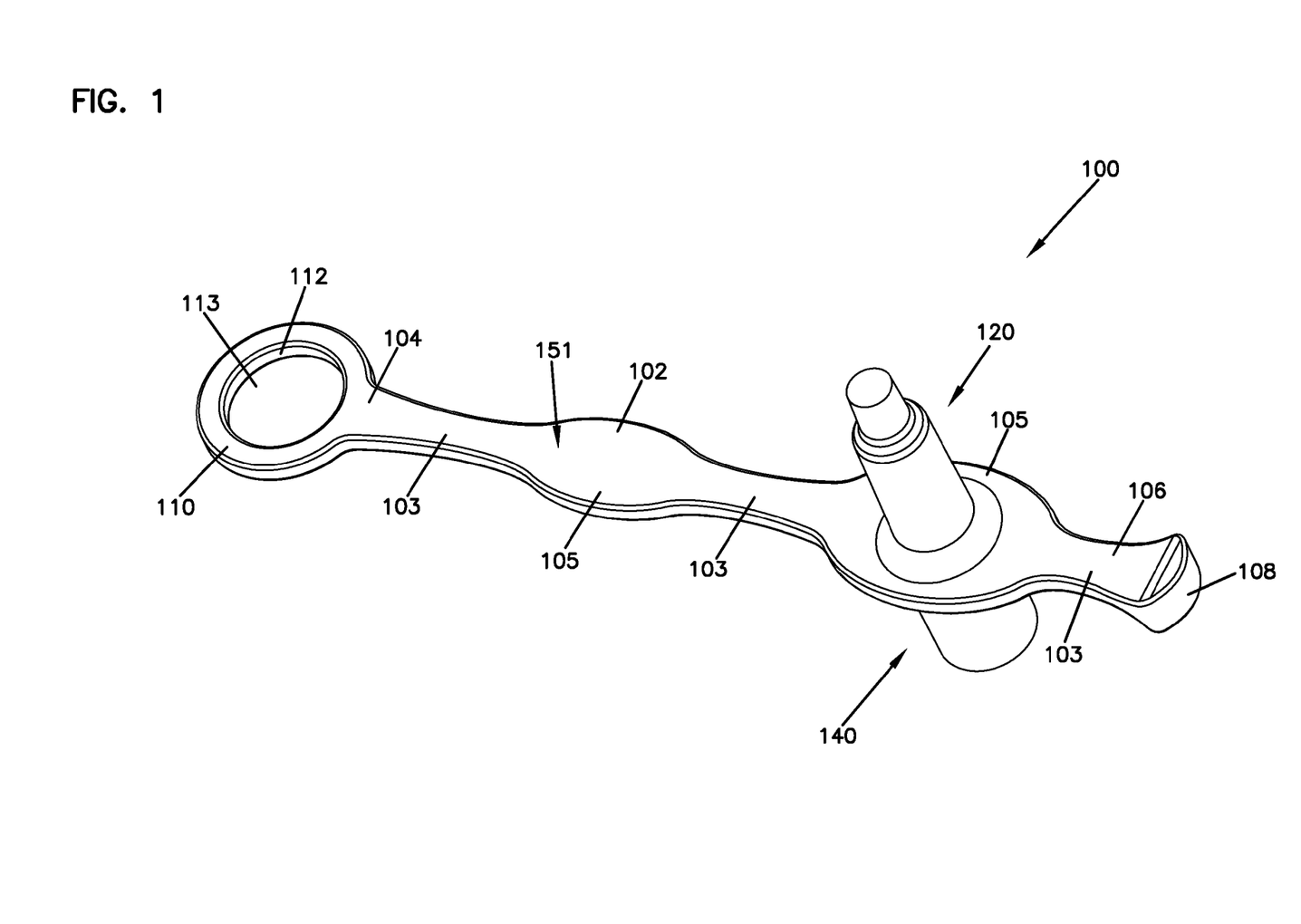
FIG. 1 is a first perspective view of an example cap and plug assembly.
Figure 2:
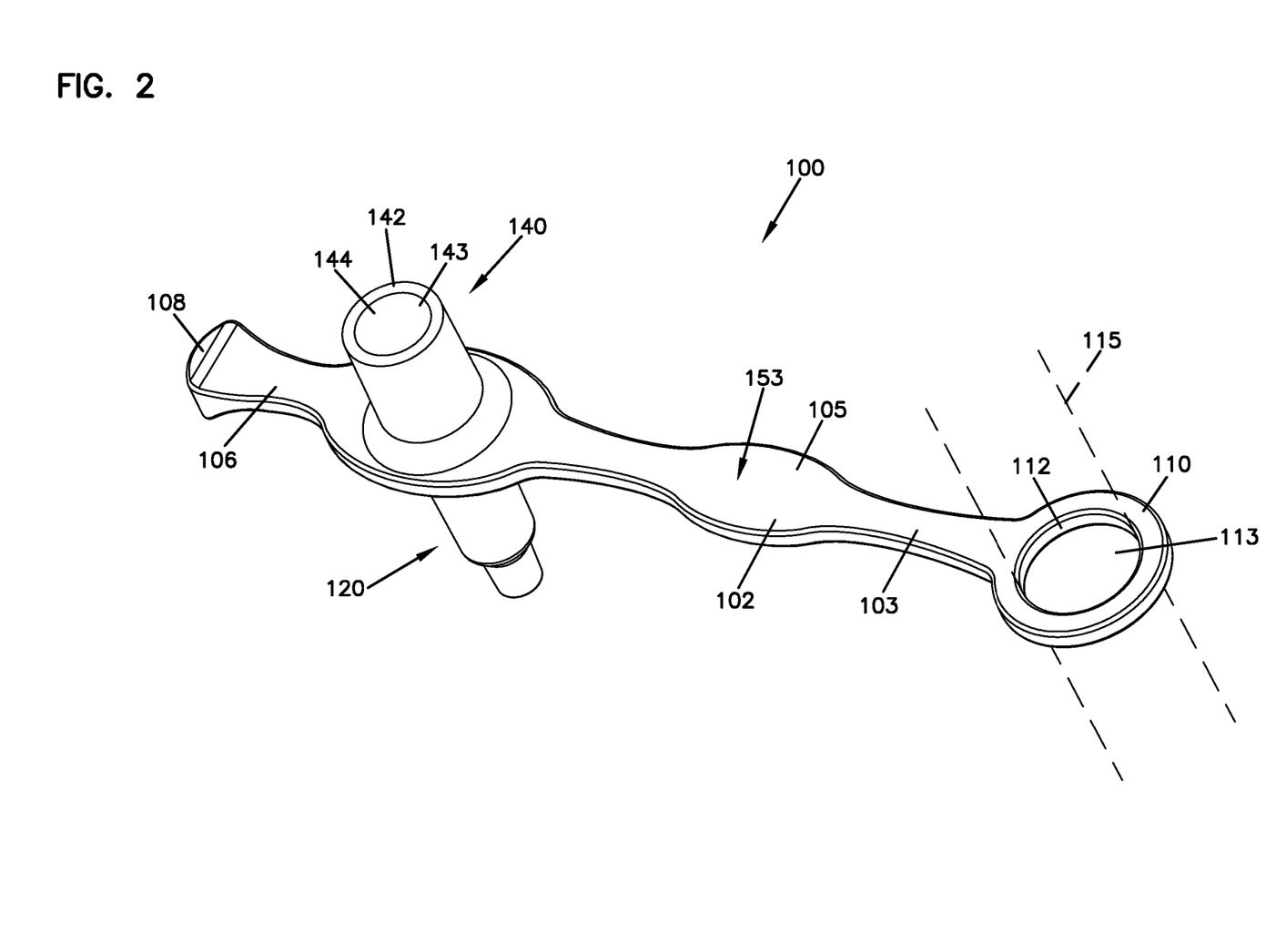
FIG. 2 is a second perspective view of the cap and plug assembly of FIG. 1.
Figure 3:
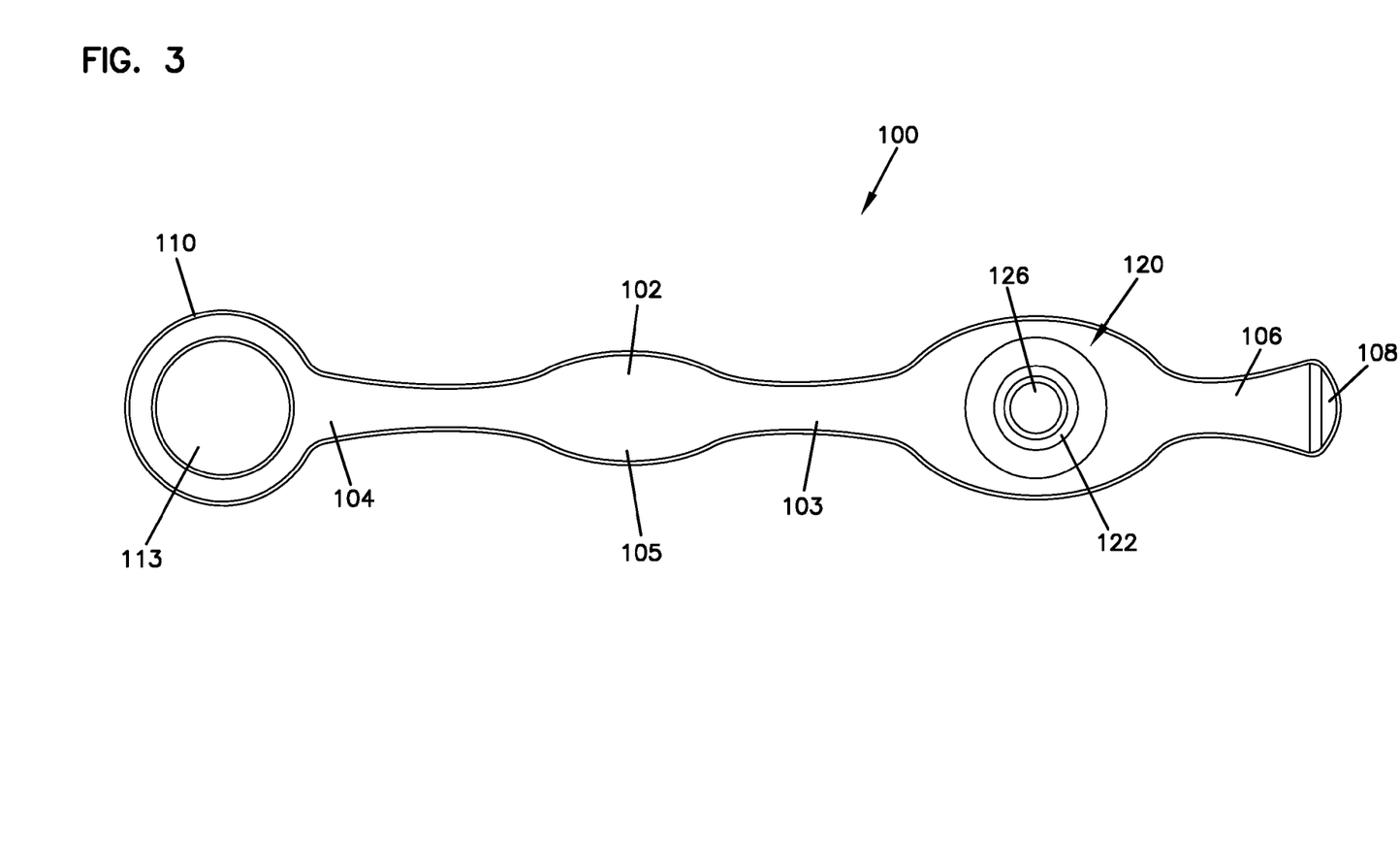
FIG. 3 is a first side view of the cap and plug assembly of FIG. 1.
Figure 4:
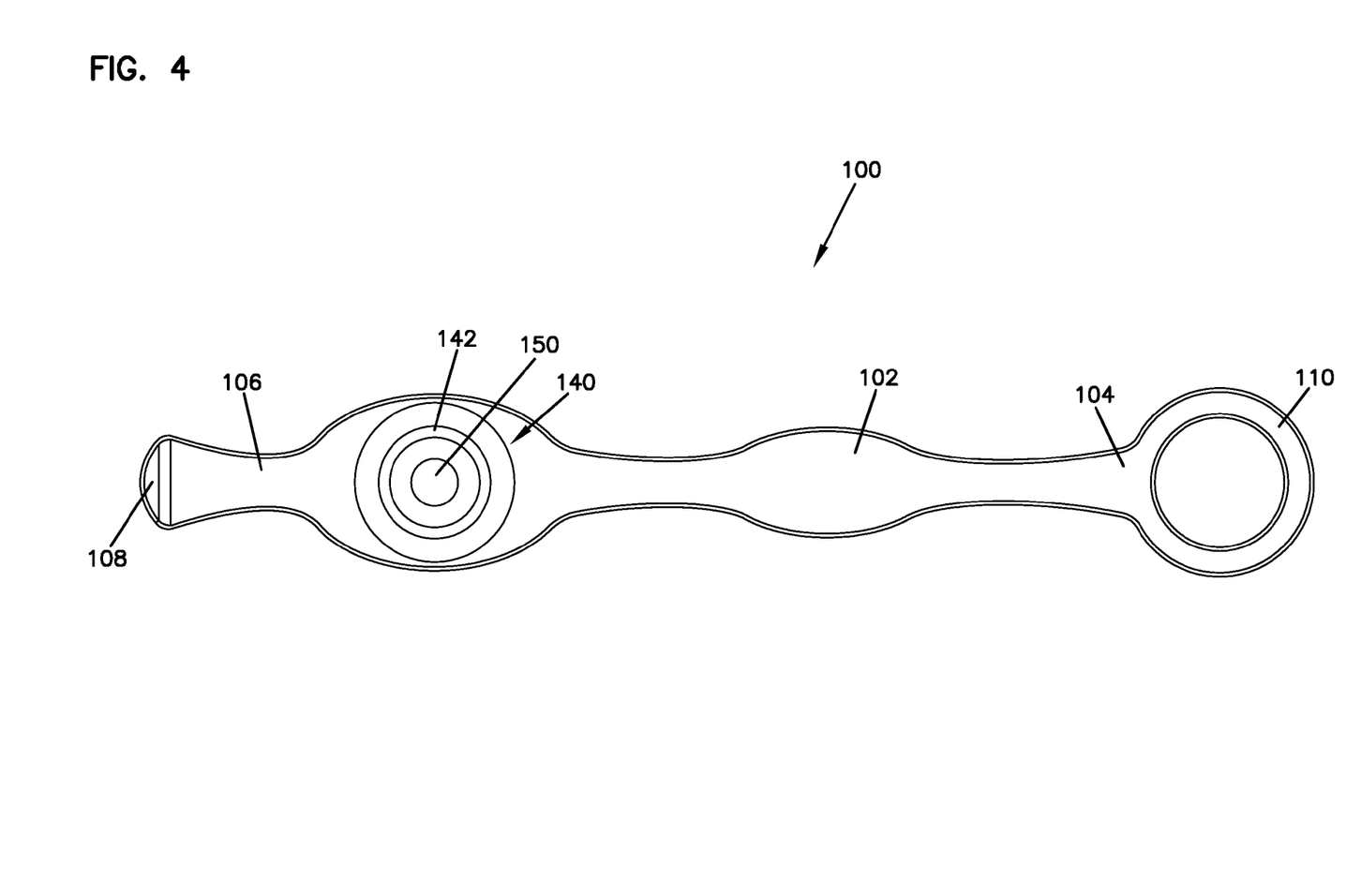
FIG. 4 is a second side view of the cap and plug assembly of FIG. 1.
Figure 5:
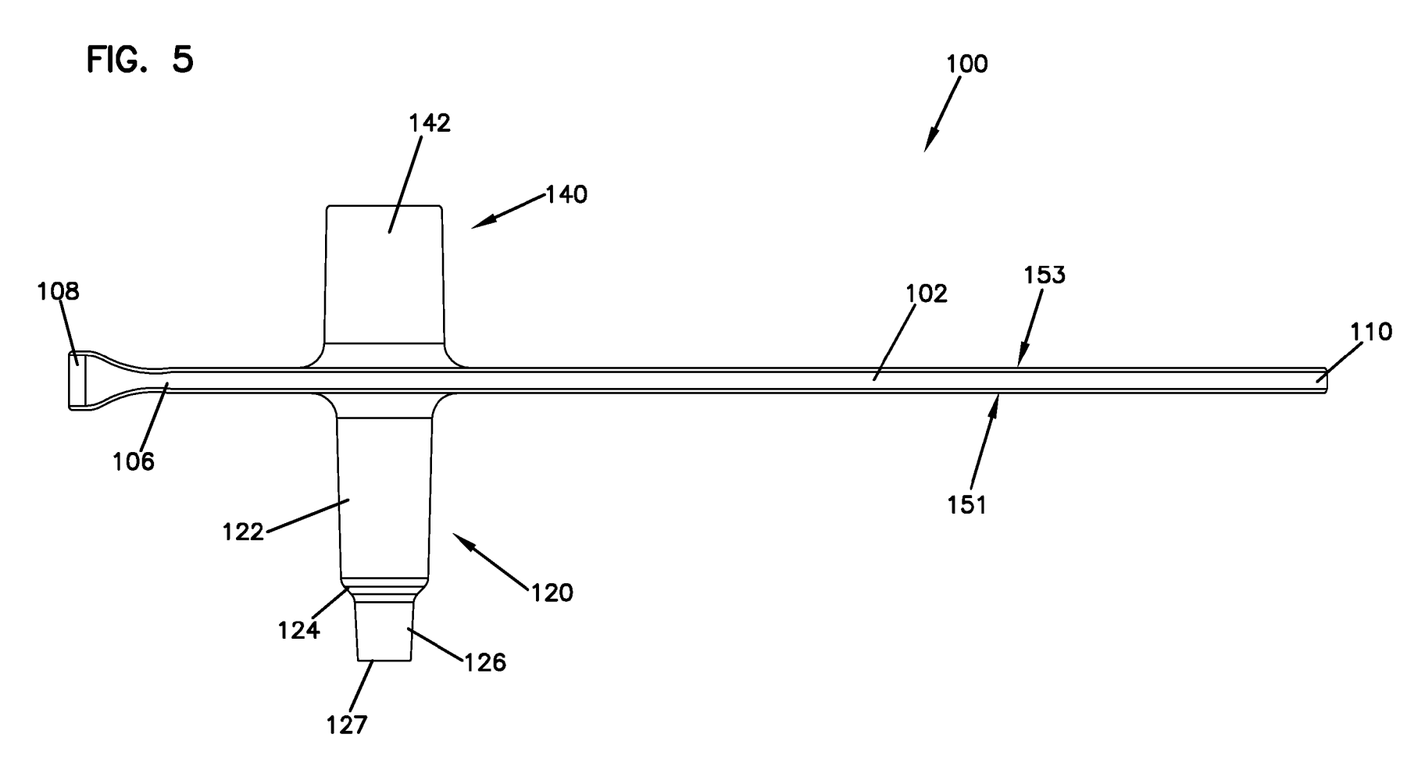
FIG. 5 is an end view of the cap and plug assembly of FIG. 1.
Figure 9:
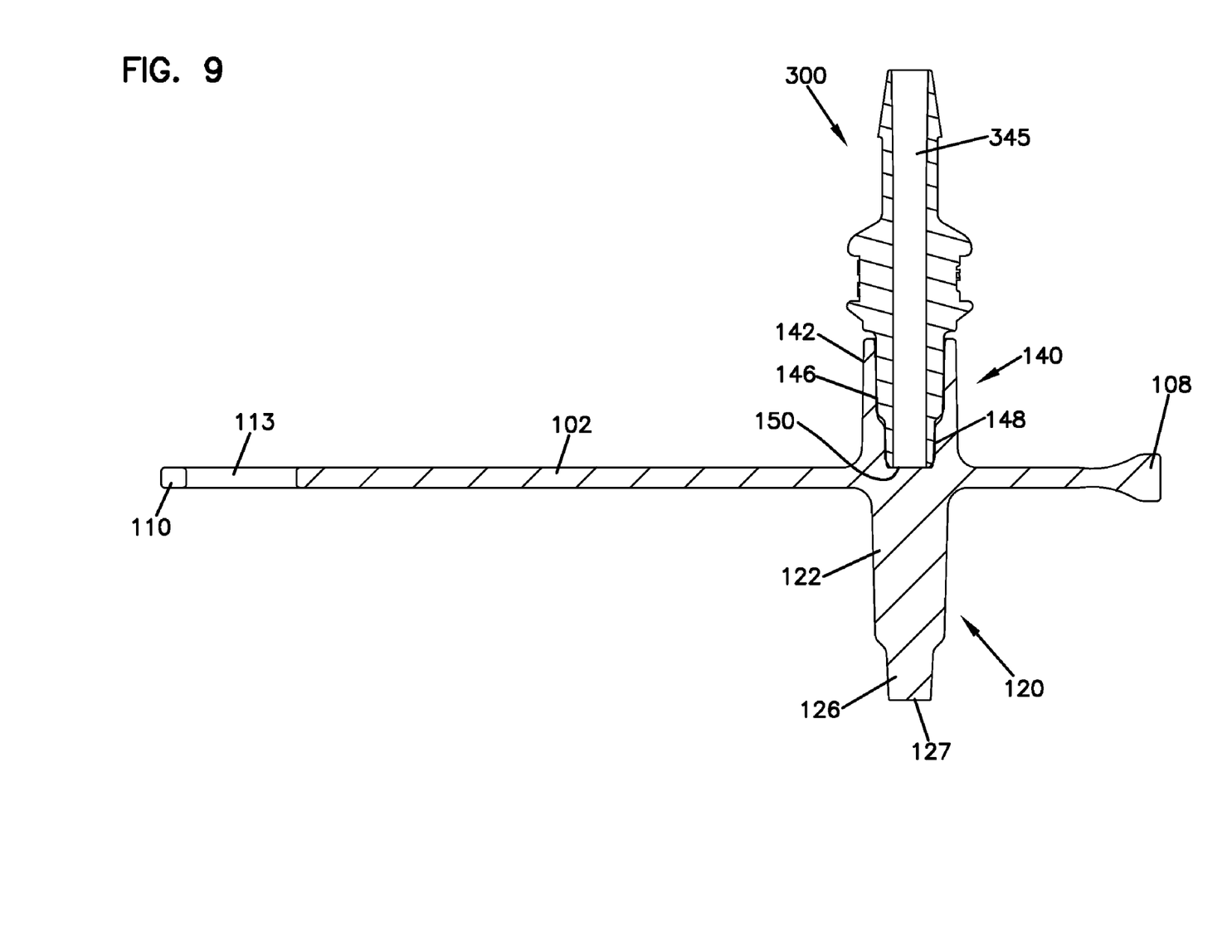
FIG. 9 is an end cross-sectional view of the male coupling of FIG. 8 with a cap portion of the cap and plug assembly of FIG. 1 placed thereon.

The cap portion 140 includes a body 142 that forms an opening 144. As shown in FIGS. 2, 4, and 9 (described further below), an interior surface 143 of the body 142 forms a first section 146 of greater diameter that transitions into a second section 148 of lesser diameter. A closed end 150 is formed at an opposite end of the second section 148. The diameters of the first and second sections 146, 148 are sized to receive a portion of a male coupling, as described below.

Referring now to FIGS. 6-9, in some embodiments the assembly 100 is used to stop the flow of material through an example female coupling 200 and/or male coupling 300.

In example embodiments, the female coupling 200 and the male coupling 300 are mated to form a continuous fluid flow path to allow the flow of fluid therethrough from a fluid source to a fluid destination. Additional details regarding the female and male couplings 200, 300 can be found in U.S. patent application Ser. No. 61/024,044 filed on Jan. 28, 2008 and U.S. patent application Ser. No. 61/040,045 filed on Mar. 27, 2008.

Figure 6:
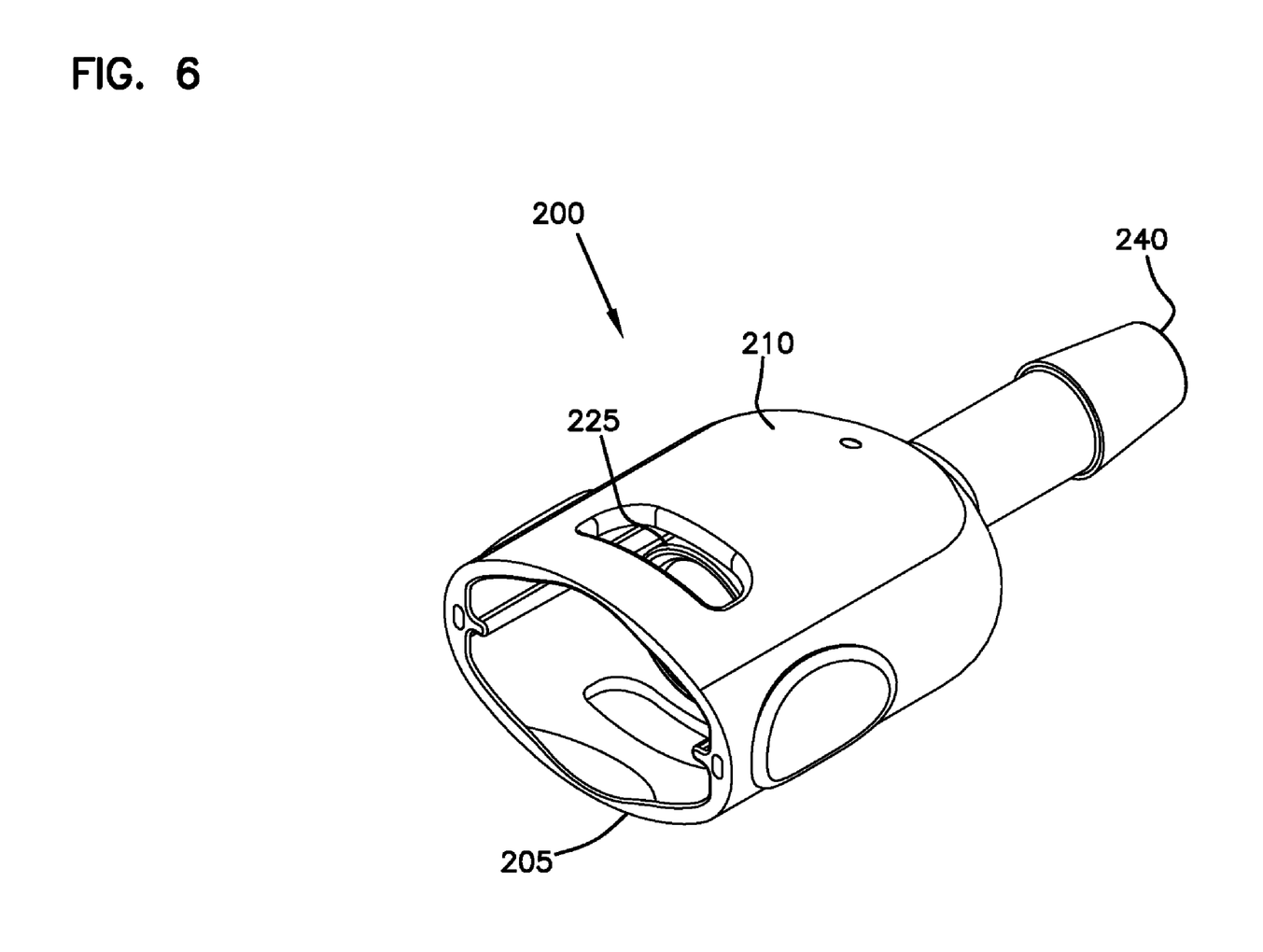
FIG. 6 is a perspective view of an example female coupling.
Figure 7:
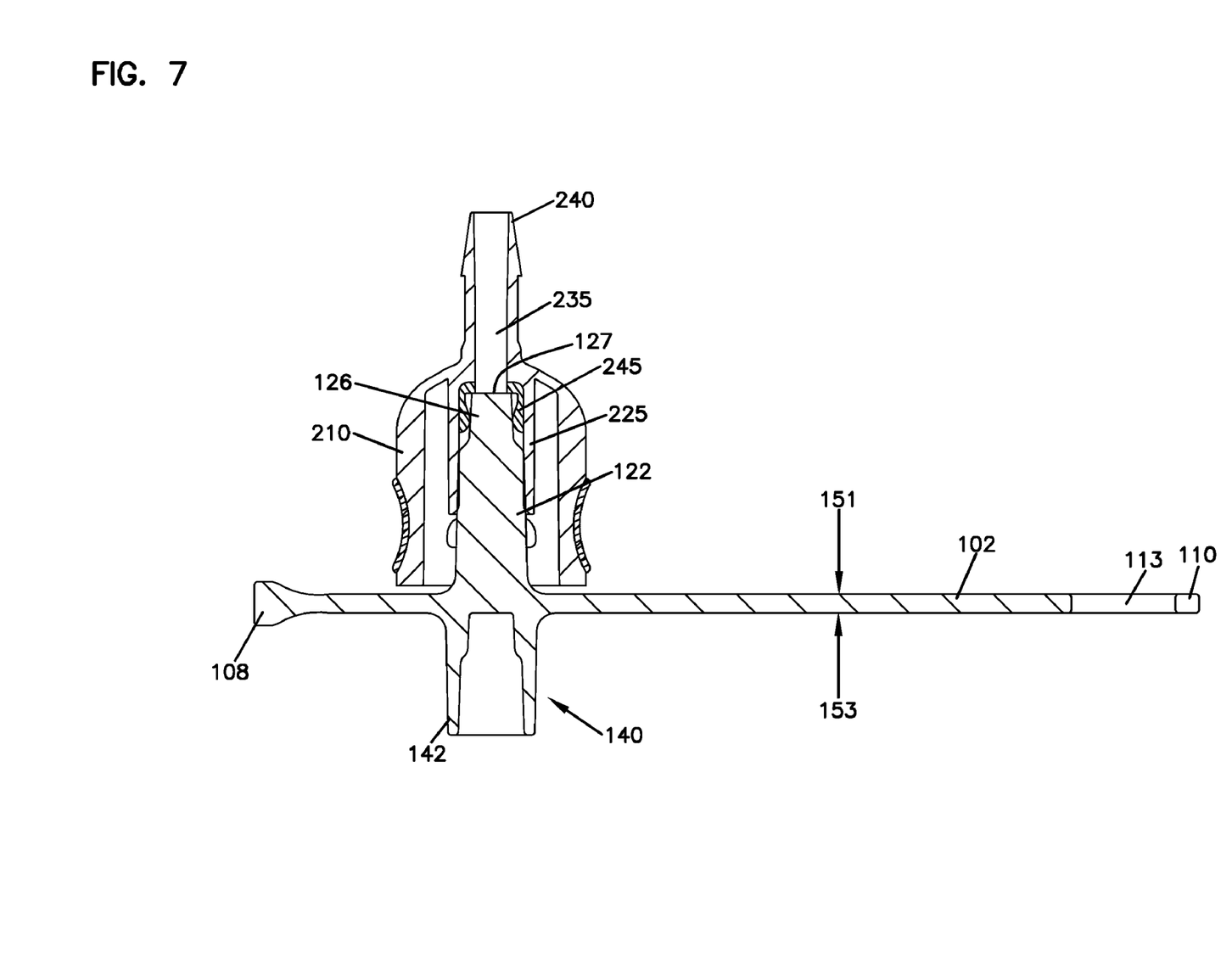
FIG. 7 is an end cross-sectional view of the female coupling of FIG. 6 with a plug portion of the cap and plug assembly of FIG. 1 inserted therein.

As shown in FIGS. 6 and 7, the female coupling 200 includes a main body 200 with a first opening aperture 205. Within the main body 200 is a lead-in receptacle 225 that facilitates the mating of the female coupling 200 with complementary structures on the male coupling 500. A female coupling fluid channel 235 is formed through the main body 200 to allow material (e.g., solids, fluids, or gases) to flow from the lead-in receptacle 225 to an end opening 240 and vice versa. A seal member 245 is formed within the lead-in receptacle 225 to seal against the mating male coupling 300.

Referring now to FIG. 7, when the female coupling 200 is disconnected from the male coupling 300, the cap and plug assembly 100 can be used to stop the flow of material from the female coupling fluid channel 235. Specifically, the end member 126 and part of the plug member 122 of the plug portion 120 are inserted into the lead-in receptacle 225. When fully inserted, the end member 126 and an end 127 of the end member 126 engage the seal member 245 to stop the flow of material from the female coupling fluid channel 235. The plug member 122 frictionally engages the lead-in receptacle 225 to retain the plug portion 120 within the female coupling 200. The volume that is defined between the end 127 and the seal member 245 is minimized to limit pooling of the material.

Figure 8:
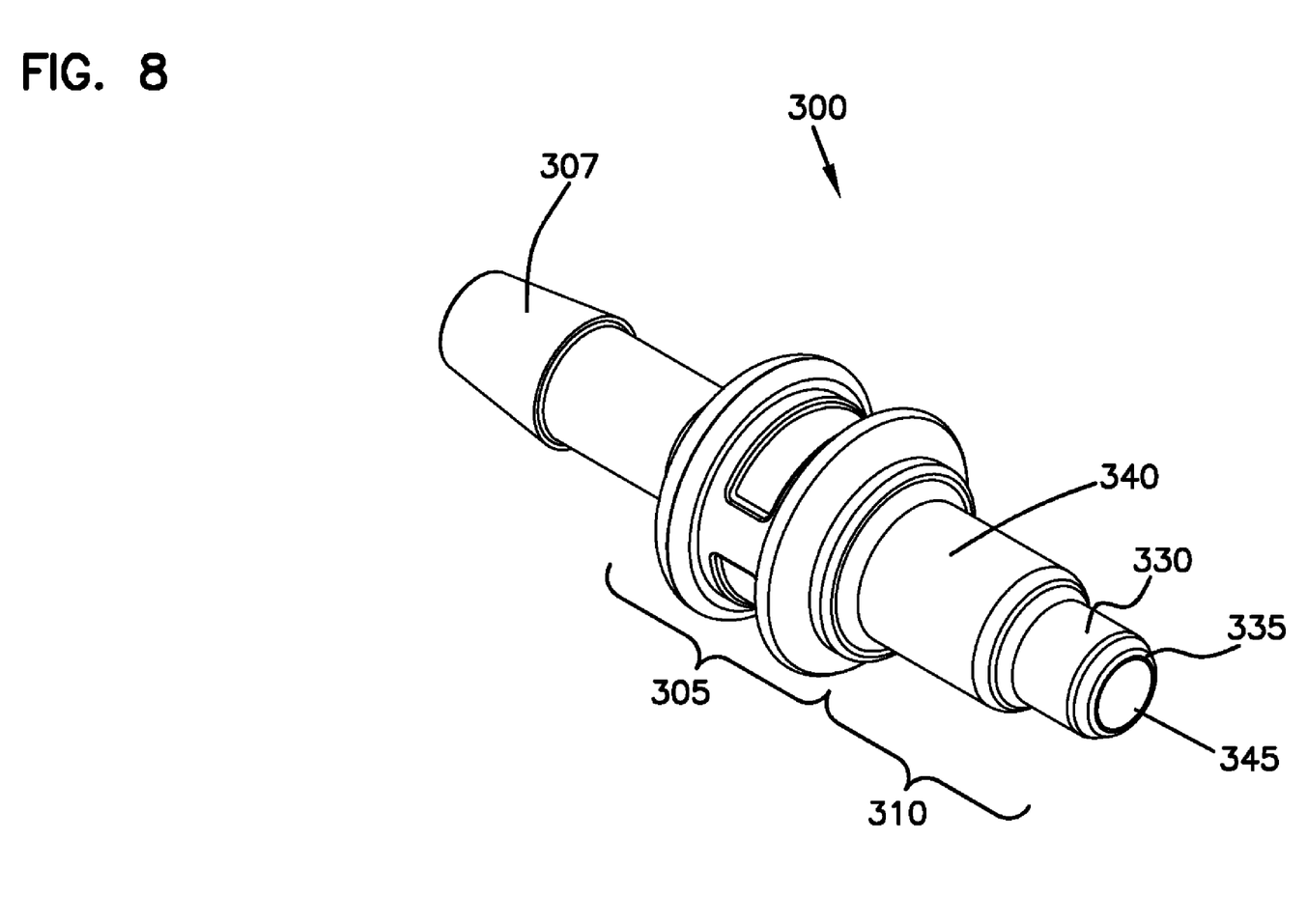
FIG. 8 is a perspective view of an example male coupling.

As shown in FIGS. 8 and 9, the male coupling 300 includes a flange member 305, a barb member 307, and an insert member 310 to facilitate the mating of the male coupling 300 with complementary structures on the female coupling 200. For example, the insert member 310 includes a primary sealing surface 335 and a secondary sealing surface 330 to facilitate sealing with the seal member 245 of the female coupling 200. An intermediate member 340 of the insert member 310 extends between the flange member 305 and the secondary sealing surface 330. A male coupling fluid channel 345 is formed through the male coupling 300.

Referring now to FIG. 9, when the male coupling 300 is disconnected from the female coupling 200, the cap and plug assembly 100 can be used to stop the flow of material from the male coupling fluid channel 345. Specifically, the secondary sealing surface 330 and part of the intermediate member 340 of the insert member 310 are inserted into the opening 144 of the cap portion 140. The insert member 310 is inserted until the primary sealing surface 335 engages the closed end 150 of the cap portion 140. In this position, the primary sealing surface 335 seals against the closed end 150, and the secondary sealing surface 330 seals against the second section 148 of the body 142 to stop the flow of material from the male coupling fluid channel 345. The secondary sealing surface 330 and the intermediate member 340 frictionally engage the first and second sections 146, 148 of the body 142 to retain the insert member 310 of the male coupling 300 within the cap portion 140. The volume that is defined between the primary sealing surface 335 and the closed end 150 is minimized to limit pooling of the material.

In example embodiments, the cap and plug assembly is used as follows. The assembly is tethered to a hose that includes a male or female coupling. Prior to connection and/or after disconnection, the user grasps the handle member or another portion of the assembly and flexes the main body of the assembly to (i) place the cap portion over the male coupling and/or (ii) insert the plug portion into the female coupling to stop the flow of material through the coupling. The assembly can be used on a single coupling, or can be used on both a male and a female coupling at the same time. The user can remove the cap portion and/or the plug portion to allow material to flow through the coupling.

In example embodiments, the cap and plug assembly is made of a material such as a thermoplastic elastomer that provides for a good seal and flexibility. In one example, a thermoplastic elastomer such as Teknor Apex Uniprene 7010-80 is used. Examples of other materials that can be used include, but are not limited to, polyvinyl chloride, polyurethane, polypropylene, thermoplastic vulcanizate (TPV), and polyethylene. Other materials can be used.

In the example shown, the cap and plug assembly is made using an injection molding process. In such an example injection molding process, a resin is heated beyond the resin's melting point and injected into a steel mold to form the assembly. Other potential methods of manufacture include, but are not limited to, machining the complete assembly, or machining (or molding) components of the assembly and bonding them together. Other methods of manufacture can be used.

In alternative embodiments, the shape and size of cap and plug assembly can be varied depending on the intended use. The geometries of the cap portion and/or the plug portion can be modified depending on the type of couplings used. For example, the dimensions of the cap and plug portions can be modified to fit couplings of different sizes and shapes. Also, the cap portion can be modified to include one or more components that are inserted into a portion of a male coupling in addition to or in place of surrounding the male coupling to stop the flow of material therethrough.

In other alternative designs, multiple cap and/or plug portions can be provided along one or both sides of the assembly so that the assembly can be used on more than two couplings at one time. In another design, the cap and plug portions can be provided on a same side of the assembly. In another alternative, the cap and/or plug portions can include members that positively engage the couplings, such as a latch that can be locked and unlocked to physically attach the cap and/or plug portions to the couplings. Other modifications can be made.

There are one or more advantages associated with the example cap and plug assemblies described herein. For example, the combination of both the cap and plug portions on the assembly allows the assembly to be used for both male and female couplings. This provides for easier use in the field. Also, manufacturing costs are reduced because a single piece performs both functions, allowing for a single tool to be used to create the assemblies at higher volumes. The tether allows the cap and plug assembly to be placed on the hose near the couplings so that the assembly is available for ready use upon disconnection of the male and female couplings.

Further, the cap and plug assembly is easy to use since the cap and plug assemblies are preferably held in place with friction within the male and female couplings. This allows the cap and plug assemblies to be inserted and removed easily while maintaining a good seal when in place. In addition, the seal of the cap portion and the plug portion is located near the flow paths of the male and female couplings, thereby minimizing the volume available for fluid to collect. This "low-spill" design provides for a cleaner plugging and unplugging process with reduced spillage.

The various embodiments described above are provided by way of illustration only and should not be construed to limiting. Various modifications and changes that may be made to the embodiments described above without departing from the true spirit and scope of the disclosure.

What is claimed is:

1. A system for restricting flow of a material, comprising:
   at least one tube;
   a male coupling, comprising:
      a male coupling fluid channel formed therein to allow a first material to flow therethrough,
      a flange member, and
      an insert member including a primary sealing surface, a secondary sealing surface, and an intermediate member extending between the flange member and the secondary sealing surface;
   a female coupling, comprising
      a female coupling fluid channel formed therein to allow a second material to flow therethrough, and
      a seal member formed within a lead-in receptacle; and
   a combination cap and plug assembly, comprising:
      a main body including first and second ends and first and second sides;
      a tether member positioned at the first end, the tether member defining an opening sized to receive the at least one tube;
      a cap portion positioned adjacent the second end and extending from the first side of the main body, the cap portion defining an opening sized to receive a portion of the male coupling and configured to restrict flow of the first material through the male coupling fluid channel; and
      a plug portion positioned adjacent the second end and extending from the second side of the main body, the plug portion including a body sized to be at least partially inserted into the female coupling and configured to restrict flow of the second material through the female coupling fluid channel.

2. The system of claim 1, wherein the cap portion comprises an interior surface defining a first section of greater diameter transitioning into a second section of lesser diameter and a closed end formed at an opposite end of the second section, the diameters of the first and second sections sized to receive complementary portions of the male coupling, and wherein the plug portion comprises a plug member of greater diameter transitioning into an end member of lesser diameter.

3. The system of claim 2, wherein the secondary sealing surface and part of the intermediate member of the insert member are positioned into the opening of the cap portion to restrict flow of the first material through the male coupling fluid channel, wherein the primary sealing surface engages the closed end of the cap portion such that the primary sealing surface seals against the closed end and the secondary sealing surface seals against a second section of the cap portion.

4. The system of claim 2, wherein the end member and part of the plug member of the plug portion are positioned into the lead-in receptacle of the female coupling to restrict flow of the second material through the female coupling fluid channel, wherein the end member and an end of the end member engage the seal member formed within the lead-in receptacle.

* * * * *